United States Patent [19]

Hoots et al.

[11] Patent Number: 5,411,889
[45] Date of Patent: May 2, 1995

[54] REGULATING WATER TREATMENT AGENT DOSAGE BASED ON OPERATIONAL SYSTEM STRESSES

[75] Inventors: John E. Hoots, St. Charles; Martin R. Godfrey, Elburn, both of Ill.

[73] Assignee: Nalco Chemical Company, Naperville, Ill.

[21] Appl. No.: 194,679

[22] Filed: Feb. 14, 1994

[51] Int. Cl.6 ............................................. G01N 21/64
[52] U.S. Cl. .......................................... 436/6; 436/52; 436/79; 436/80; 436/84; 436/163; 436/172
[58] Field of Search ................. 436/52, 56, 6, 84, 166, 436/164, 172, 800, 79, 80, 163; 422/62

[56] References Cited

U.S. PATENT DOCUMENTS

| | | | |
|---|---|---|---|
| 4,783,314 | 11/1988 | Hoots et al. . | |
| 4,963,267 | 10/1990 | Hoots et al. . | |
| 4,966,711 | 10/1990 | Hoots et al. . | |
| 4,992,380 | 2/1991 | Moriarty et al. | 436/55 |
| 5,006,311 | 4/1991 | Hoots et al. | 436/62 |
| 5,035,806 | 7/1991 | Fong et al. . | |
| 5,041,386 | 8/1991 | Pierce et al. . | |
| 5,128,419 | 7/1992 | Fong et al. . | |
| 5,132,096 | 7/1992 | Hoots et al. . | |
| 5,171,450 | 12/1992 | Hoots . | |
| 5,200,106 | 4/1993 | Hoots et al. . | |
| 5,216,086 | 6/1993 | Fong et al. . | |
| 5,236,845 | 8/1993 | Pierce et al. | 436/6 |
| 5,260,386 | 11/1993 | Fong et al. . | |
| 5,266,493 | 11/1993 | Young . | |
| 5,277,135 | 1/1994 | Dubin et al. . | |
| 5,278,074 | 1/1994 | Rao et al. | 436/52 |
| 5,282,379 | 2/1994 | Harder et al. . | |

*Primary Examiner*—Jeffrey R. Snay
*Attorney, Agent, or Firm*—Robert A. Miller; James J. Drake

[57] ABSTRACT

A target-specie responsive regulation of water treatment agent feed is achieved by the monitoring of a subject target-specie indicator. A target specie in a sample taken from the system is selected as the subject target-specie indicator, or instead an incipient reagent is added to the system sample to form a subject target-specie indicator. Such a formed subject target-specie indicator comprises a combination of the incipient reagent and a target specie. The subject target-specie indicator might then monitored by fluorescence analysis of the sample to determine at least one fluorescence emission value that can be correlated to the in-system concentration of the target specie. In combination with an inert tracer, the system consumption for the target specie can be determined. A responsive adjustment of the in-system concentration of a water treatment agent can be made.

16 Claims, No Drawings

REGULATING WATER TREATMENT AGENT DOSAGE BASED ON OPERATIONAL SYSTEM STRESSES

TECHNICAL FIELD OF THE INVENTION

The present invention is in the technical field of regulating the in-system concentration of water treatment agents and/or system operation, particularly the in-system concentration of water treatment agents in industrial water systems, such as cooling water systems, boiler water systems, water reclamation/purification systems, water systems of manufacturing processes and the like, by analysis of target specie(s) in the system, particularly scaling ions and contaminants, so as to increase the efficiency of the water treatment agents and/or operation of systems in which they are used.

BACKGROUND OF THE INVENTION

The in-system concentration of water treatment agents in industrial water systems is conventionally controlled based on intermittent measurements of the concentration of the target specie(s) and/or the concentration of the water treatment agent(s) in the water of the system or unselective measurements (e.g., conductivity). The control goal of most water-treatment programs is to maintain a predetermined or optimum ratio of water treatment agent(s) to target specie(s) (for instance scaling ions, contaminants and the like) in the water of the system. The in-system concentration of the water treatment agent(s) is regulated to attain or maintain this ratio or the target specie concentration is adjusted to meet specified values. For instance, if the concentration of hardness ions entering a boiler system increases, an increase in the in-system concentration of the water treatment agent(s) may be needed to maintain the water treatment agent(s) to target specie(s) ratio goal. The measurements of the concentration of the target specie(s) and/or the concentration of the water treatment agent(s) in the water of the system, and the responsive in-system concentration adjustments, are commonly based only on occasional grab samples, taken for instance once or twice per shift (a shift commonly encompassing about 8 to 12 hours of system operating time) or once every several days. Concentration determinations for water treatment agents and/or target species in industrial water systems have heretofore generally been based on classical (wet chemistry) analysis techniques, conductivity and/or hydraulic meter readings, for instance water flowmeter readings.

Classical analysis techniques for determining the concentration of a target specie and water treatment agents in a water system are usually somewhat cumbrous and/or protracted, and/or provide results that are merely estimates and/or variable (for instance, dependent upon a person's laboratory technique). Long time delays typically exist between changes in system operation and a compensating change in treatment dosage. For example, phosphate concentrations are determined by a spectrophotometric (colorimetric) test. Concentrations of pyrophosphate and organic phosphorus compounds are determined using the same spectrophotometric test with a digestion (reversion) step. Titration methods are routinely employed to determine the concentration of hardness ions, such as calcium and magnesium, and the concentrations of carbonate and bicarbonate, in the water of the water system. Such analysis methods are susceptible to interferences (e.g., turbidity) and/or are subjective (visual observation of color change). These values, and often the ratio therebetween, are then used to manually set the in-system target concentration of the treatment chemicals, such as scale inhibitors and neutralizing amines.

The more accurate a conventional manual (grab sample) analysis technique, the more protracted that technique or its response time can be. Feedback information can at times even be days behind the sampling and hence of little value in providing data from which a dosage-regulation response can be determined. The water system consumption of a water treatment agent may well have changed during the elapsed interval between the taking of the sample and the analysis results.

Even when accurate indications of the mass or volume of a water treatment agent feed delivered to a system are available, and accurate water treatment agent residual concentrations are available, if the residual concentration determinations are based on grab or intermittent samples, any extrapolation therefrom to a value for the system demand and/or system consumption for the water treatment agent is based on fragmentary data and outdated information. A change in the system consumption may not be detected until it has had a significant impact on treatment agent consumption and system performance. When the detection of system consumption change is delayed, the responsive regulation of a treatment agent's in-system concentration or response to system operation will invariably be late and system performance may suffer. When the responsive regulation of in-system concentration is late, underfeeding or overfeeding of the treatment agent routinely will occur to some extent between the time the system consumption of the water treatment agent has changed and the time the treatment agent in-system concentration and/or system operating parameter (e.g., alkalinity adjustment) is adjusted.

In an industrial water system plant the use of any estimated, variable, intermittent, fragmentary or historic data severely diminishes the sensitivity of any demand-responsive regulation of the water treatment agent in-system concentration and/or diminishes the ability to follow changes in the treatment-agent system demand or system consumption with appropriate compensations to the water treatment agent in-system concentration.

Conventional procedures for regulating water treatment agent in-system concentration are further complicated by other imprecise evaluations of operating parameters. The rates at which the water treatment agent is being fed to and/or removed from the industrial water system and/or other operating parameters having an influence on the in-system concentration of the water treatment, may defy precise measurement unless inert tracers and selective analytical methods are used. The readings and/or settings on feed and blowdown equipment and/or lines are seldom unquestionably reliable and often complicated by multiple sources of blowdown and makeup and changes in composition of these water samples. Fluctuations in the concentrations in the target species and the water treatment agent may stem from a variety of system conditions, such as dilution when other materials are charged to the system, concentration by evaporation or other means, unaccounted loss of fluid from the system and the like, some of which parameters may not be accurately known. Generally all sources of water intake and loss, and all sources of water treatment agent intake and loss, cannot be known precisely and continuously unless inert tracers and selective analytical methods are used.

A sensitive, selective and rapid demand-responsive control of water treatment agent in-system concentration would render most any industrial water system more efficient. Overfeeding of a water treatment agent is unnecessarily expensive, may at times diminish the recycling potential of waste water discharged from the system and may also at times impair system operation. Underfeeding of a water treatment agent almost inevitably impairs system operation, the imbalance between an underfed water treatment agent and the target species leading to higher levels of deleterious effect(s) from which relief is sought by the water treatment. In some water systems an imbalance between the in-system concentrations of water treatment agents and the system's water conditions and/or target species can severely diminish the efficiency of the system. For instance the efficiency of a system's temperature conditioning performance, such as heat exchange and steam generation, may be reduced which in turn may diminish the performance of a process to which it is adjuvant.

A sensitive, selective and rapid demand-responsive regulation of water treatment agent in-system concentration that permits the in-system concentration of water treatment agent(s) to be adjusted in response to real-time system conditions is not provided by the conventional methods.

It is an object of the present invention to provide a method or process for monitoring the concentration of a target specie(s) in a water system, thereby permitting a responsive regulation of the in-system concentration of one or more water treatment agents and/or adjustment of system operating parameters (e.g., alkalinity, etc.) It is an object of the present invention to provide such a method or process that can be conducted on-site in a very short time period. It is an object of the present invention to provide such a method or process further including the regulation of the in-system concentration of at least one water treatment agent and/or system operating parameter in an industrial water system in response thereto. It is an object of the present invention to provide such a method or process that can be conducted on-site in a very short time period, preferably on a continuous basis. It is an object of the present invention to provide in an industrial water system one or more monitorings of target specie(s) on-site in a very short time period, preferably on a continuous basis. These and other objects of the present invention are discussed in detail below.

SUMMARY OF THE INVENTION

The present invention provides a demand-responsive management (regulation or control) of water treatment agent in-system concentration(s) and/or system operating parameter(s), for instance by regulating water treatment agent feed, which includes the monitoring of the value of a target-specie indicator, preferably by fluorescence analysis. The present invention provides a process for the regulation of at least one water treatment agent in-system concentration and/or system operating parameter, based on the value of at least one target specie for that treatment agent and/or operating parameter, comprising monitoring a fluorescent characteristic of at least one target-specie indicator that is itself a target specie or is a combination of an incipient reagent and a target specie. The target specie for instance may be a chemical specie, sealants, corrosion products, corrosive agents, foulants or a water condition, such as pH, that is targeted by the treatment agent, that is, indicia of system demand and/or system consumption for a water treatment agent or scaling/deposit forming, fouling, or corrosive conditions. In more detail, the target specie may be a chemical specie that is produced by another chemical specie or by a water condition, for instance corrosion products. The target specie may be a system-demanding and/or system consumption condition, for instance system pH. The target specie may be other types of indicia of system consumption for a water treatment agent that itself is, or in combination with a suitable reagent forms, a target-specie indicator having a fluorescent characteristic which can be correlated to the value of the target specie. That fluorescent characteristic is monitored, preferably on a continuous basis, by at least one fluorescence analysis method and the results of such monitoring preferably are correlated to a regulation of the in-system concentration of such treatment agent and/or system operating parameter. According to other preferred embodiments of the invention, the target-specie is monitored by other election means, including, but not limited to, light absorbance, chemiluminescence and ion-selective electrode.

The present method also provides a demand-responsive management (regulation or control) of water treatment agent in-system concentration based on system demand for the target specie. In preferred embodiments, the present invention further includes the monitoring of an inert tracer, which together with the monitoring of the target-specie indicator is used to determine system demand for the target specie, which is described in detail below.

In further preferred embodiments, the effects of target-specie responsive adjustments to the treatment agent's in-system concentration are tracked by a continuous monitoring of the target-specie indicator, preferably in combination with a continuous monitoring of an inert tracer, which is described in detail below.

PREFERRED EMBODIMENTS OF THE INVENTION

The system consumption for any specie (subject specie) added to a system in known proportion with an associated inert tracer can be determined from the following Formula.

Formula $C_1 - C_2 = SC$ wherein $C_1$ is the theoretical subject specie concentration determined by correlation to the concentration of an associated inert tracer (added in known proportion with the subject specie), $C_2$ is the actual concentration of the subject specie in the system, and SC is the system consumption upon the subject specie or, in other words, selective impact(s) upon in-system concentration of the subject specie that does not effect the inert tracer's in-system concentration.

A sensitive and rapid target-specie responsive control of water treatment agent in-system concentration is provided by the on-line continuous monitoring of the value of a target-specie indicator in the water system. The on-line continuous monitoring of the value of a target-specie indicator, for instance a target specie(s) concentration, provides precise and accurate results rapidly and permits the in-system concentration of the water treatment agent(s) and/or operating parameters to be adjusted in response thereto. The in-system concentration of a water treatment agent or a plurality of water treatment agents can be adjusted by regulation of the rate of feed or delivery of the agent(s) to the system, by regulation of the ratio between rate of delivery versus rate of removal with blowdown and/or the regulation of any means influencing the in-system concentration the water treatment agents.

The present invention includes the monitoring of the value of a target specie in the water of an industrial water system. By the terminology "monitoring of a target specie" is meant herein, unless expressly indicated otherwise, the determination of at least one fluorescence characteristic of a target-specie indicator in a sample from a water system and the correlation of that characteristic to a value designating the proportion or degree of the target specie in the water system, such as the concentration of a scaling ion or the pH value of the water. That value can in turn be correlated to specified dosage or system consumption for a water treatment agent. By the terminology "regulating" is meant herein, unless expressly indicated otherwise, the setting and/or the adjustment of a system control means, for instance the feed rate of the water treatment agent to a water system, which determines at least in part the in-system concentration of the treatment agent. Such monitoring and/or regulating can be conducted on a singular, intermittent, semi-continuous or continuous basis, and preferably at least the monitoring, and more preferably both the monitoring and regulating, is/are conducted on-site (at the site of the industrial water system plant) on a substantially continuous basis.

By the terminology "in-system concentration" is meant herein, unless expressly indicated otherwise, the concentration of the subject specie within the water phase of the subject water system, generally as a solute. An in-system concentration of a water treatment agent or target specie, for instance, does not include any amounts thereof that are contained in scale deposits or other solid phase material even if such materials are within the confines of the water system.

The present invention includes the regulating of the in-system concentration of at least one water treatment agent based on the system consumption for the treatment agent by employing the information provided by the monitoring of the target-specie indicator. The water treatment agent in-system concentration and/or operating parameter is regulated by the process of the present invention based on the present value of a target specie within the industrial water system, and not on estimated, fragmentary or historic data. Since the present invention directly monitors a target-specie indicator, which is, or is correlated to, a target specie, it can be considered a method that tracks, and/or obviates the need to quantify, the multitude of influences on the water treatment agent system demand and/or system consumption, such as the introduction of the target specie to the system with makeup water or other added materials, mixing of multiple streams, contamination, leaks between systems, leaks from the system, other dilutions and concentrations, releases of target specie(s) into the water from known and unknown sources, losses of target specie(s) from the water by known and unknown mechanisms and the like.

The value of a target-specie might alter by system variations independent of treatment agent in-system concentration. In other words, a given treatment agent in-system concentration may be wholly meeting the demands of a target-specie for a time period, and then the value of that target-specie could rapidly change in response to other system variables. An increase in the target-specie in such instance is not an indication that the initial treatment agent in-system concentration was inadequate, and instead is a signal that the water system now requires a higher treatment agent in-system concentration. A decrease in the target-specie similarly could a signal that continuing the initial treatment agent in-system concentration would be an overfeeding, or instead be a signal that the treatment agent in-system concentration is too low, as described below.

Variations in the system consumption can occur by virtue of numerous operating conditions. The rate at which the target specie is entering and/or leaving and/or being generated in an industrial water system cannot wholly be predicted or controlled. An industrial water system commonly has unknown sources of material intake and/or losses and/or chemical conversions. The optimal monitoring of such target specie(s) and/or operating parameter(s) is to quantify their concentration or degree in a water system, rather than attempting to estimate its change in concentration or degree based on other parameters. The method of the present invention can determine the concentration of one or more target specie(s), or other target specie value, from the target-specie indicator value that can be correlated thereto, using one or more fluorescence analysis techniques.

The present invention provides target-specie responsive treatment agent in-system concentration adjustments that are not contingent on water treatment agent residual level determinations, although also performing the analyses necessary for water treatment agent residual level determinations is not excluded. In broad embodiments the present target-specie responsive in-system concentration adjustments are not even dependent upon the use of an inert tracer and/or traced water treatment agent feed.

The water treatment agent in-system concentration is regulated so as to be responsive to the fluorescent characteristic of the target-specie indicator and/or operating parameter(s) at the sampling site(s), which in turn is correlated to the target specie value, which is proportional or inversely proportional to system demand and/or system consumption for that water treatment agent. A target specie is selected so that its value is proportional/inversely proportional to, or convertible in some respect to, system consumption for (or required dosage of) a water treatment agent. For the purposes of the present invention, a suitable target specie(s), or other target specie for a given water·treatment agent, is one that can be correlated to the system consumption for (or required dosage of) that treatment agent. For example, when the treatment agent is an antiscalant, for instance a dispersant, a specie such as calcium and/or iron would be an appropriate target specie. The calcium and/or iron concentrations in a system are correlated to the scaling tendencies or loss of treatment agent within the water of the system, and either calcium or iron concentrations, or both in combination, are useful corollaries of system consumption for antiscalant treatment agent.

According to one embodiment of the invention, the monitoring of a target specie is preferably also used to determine the system consumption for such target species. For instance, the concentration of calcium ions in makeup water being introduced to a water system is determined. Adding an inert tracer to the water system in proportion to the calcium ions, for instance by adding the inert tracer with the makeup water, provides a means for readily determining zero-consumption concentration of the calcium ions in the water system. The actual concentration of calcium ions in water being charged to and discharged from the system can also be readily determined by analysis for its target-specie indicator. The monitoring of the calcium-ion indicator to determine the in-system concentration of calcium ions, particularly in combination with the monitoring of an associated inert tracer, may show a selective loss of calcium ions from the water of the system. The actual calcium ion concentration in the system is less than the zero-consumption concentration value indicated by the inert tracer concentration. Such system consumption of calcium ions may be due to scale formation or an excess of calcium ions may result from dissolution of scale.

The existence of such system consumption for a target specie may be very undesirable, and its detection would alert an operator that scale formation preventive measures must be increased. On the other hand, in some instances, the existence of such system consumption for a target specie may be desired, for instance where the reduction of the in-system concentration of the target specie by precipitation, flocculation or particulate formation in a certain system is the objective. In either case, the effect of any responsive adjustment of in-system concentration of a treatment agent can be tracked by continuing the comprehensive target specie monitoring. The effectiveness of a treatment that dissolves scale deposits and/or inhibits scale formation would be seen as an increase in the in-system concentration of calcium ions and/or a decrease in the system consumption for calcium ions. The effectiveness of a treatment that promotes precipitation, flocculation or particulate formation would be seen as a decrease in the in-system concentration of calcium ions and/or an increase in the system consumption for calcium ions.

Another type of target specie is related to destructive treatment agent consumption, for instance by degradation, complexation, precipitation and the like phenomena. System contaminants such as hydrogen sulfide can adversely affect performance of treatment agents and thus be correlated to system consumption for (or required dosage of) the treatment agent. Thus hydrogen sulfide and other destructive chemical species and/or water conditions may be apt candidates for the role of monitored target specie in some systems.

Substances that exhibit fluorescence characteristics are referred to as fluorophores. Fluorophores are generally aromatic organic compounds and/or complexes. Some inorganic ions of heavy elements, such as the lanthanides, have fluorescent properties and may serve as useful fluorophores for the present invention. Most simple inorganic ions, however, themselves possess no fluorescence properties. In combination with suitable fluorophores or fluorophore precursors, however, the concentrations of nonfluorescent inorganic ions can be determined by fluorescence analysis techniques. The nonfluorescent inorganic ions in this example are the target species, while the effective or final fluorescence reagent is the target-specie indicator, generated by the combination of a target specie with an incipient or first reagent.

The incipient reagent may or may not itself be fluorescent. The target-specie indicator may or may not itself be fluorescent. If both the incipient reagent and target-specie indicator are fluorescent, then the fluorescence analysis technique, including at times the selection of excitation and/or emission wavelengths, is selected to avoid, or at least minimize, interference between any residual incipient reagent and the target-specie indicator. Examples of various combinations of target specie and incipient reagents, and selections of suitable fluorescence analysis techniques for the target-specie indicators formed, are described in more detail below.

A target specie might be paired with a reagent (initial or incipient reagent) to form a target-specie indicator suitable for the fluorescence analysis technique selected, or the fluorescence analysis technique might be selected based on its suitability for the target-specie indicator.

As general examples, chemical species and/or water conditions that are commonly found in cooling waters and other industrial water systems, and are susceptible to quantification by at least one fluorescence analysis technique through the formation of a suitable target-specie indicator, include, without limitation, orthophosphates, hardness ions (calcium and/or magnesium ions), iron, fluoride, manganese, certain corrosion products, alkalinity, sulfide such as hydrogen sulfide, silica, copper, chloride, organics, sulfonates and others. Even temperature and pH are measurable by fluorescence techniques.

As general examples, chemical species and/or water conditions that are commonly found in boiler waters, and in other industrial water systems, and are susceptible to quantification by at least one fluorescence analysis technique through the formation of a suitable target-specie indicator by the present method, include, without limitation, hardness ions (calcium and/or magnesium ions), alkalinity, iron, copper, sodium, chloride, sulfate, pH, oxygen, ammonia, silica, carbon dioxide, organic acids and others.

Many of the target specie mentioned above are inorganic ions or system contaminants. Conventional analytical methods for measuring the concentration of scaling ions and system contaminants are commonly susceptible to interference. For instance, colorimetric analysis of orthophosphate is a commonly used technique mentioned above, but it is susceptible to turbidity interference and chemical interferences. Ion-selective electrode analysis for calcium ion is a commonly used technique, but it is susceptible to interference due to ionic strength changes, temperature limitations and fouling.

The process of the present invention provides an accurate determination of the degree of any changes in the system demand or system consumption for the water treatment agent and the effect of any feed rate compensations or other in-system concentration adjustments made. This information not only permits a more accurate and efficient responsive in-system concentration adjustment, but also provides an alert for upsets in the water system that will trigger an abnormal change in the water treatment agent's consumption rate. The information provided by the monitoring of the water treatment agent's target-specie indicator is of great importance to all operating parameters related to such water treatment agent.

The industrial water systems for which the present invention may be used are water systems of any industry which employs at least one water treatment agent, including without limitation temperature-conditioning water systems (wherein the waters are being used as a heat/energy transfer media), water systems wherein a raw water stream and/or water for makeup use is being purified, a water system wherein waste materials and/or waste waters are being purified, a water system wherein solids (suspended and/or solutes) are being separated from liquids (for instance the water system of membrane-separation processes), water systems of manufacturing processes, particularly chemical industry manufacturing processes, including without limitation the processes of the pulping and papermaking industries, the steel industry, the metal working industries, the food processing industries, the mining industries, the automotive industry, the textile industry, utilities, chemical processing industries, manufacturing industries, spray paint industries, refining industries such as the refining of aluminate, and the like.

Industrial water systems often are fluid systems that contain at least about 60 weight percent water, the remainder being solids (suspended and/or dissolved) and/or nonaqueous fluids, and which commonly are flowing rather than static. In preferred embodiment the industrial water system of the present invention is an industrial system that contains at least about 65 or 70 weight percent water, the remainder being solids (suspended and/or dissolved) and/or nonaqueous fluids, and preferably which is flowing rather than static.

The present invention in broad embodiment, however, is not limited to industrial water systems, and instead may be applicable to nonaqueous fluid systems. There are instances of the use of water treatment agents in substantially nonaqueous fluid systems. For instance, neutralizing amines are used in some hydrocarbon streams in the oil refining industry. It may be highly beneficial to monitor the concentration of chlorides, other anions and/or other impurities in such hydrocarbon streams for the purpose of the present invention, i.e., regulating treatment agent. The process of the present invention may be employed for mixed aqueous/nonaqueous fluid systems and nonaqueous fluid systems in the same manner as in aqueous systems, provided any potential interference with the fluorescence analysis arising from the nonaqueous portion of the fluid can be avoided. Since the present invention is believed to be most readily and commonly adaptable to water systems, for simplicity but not for limitation purposes the invention is described herein in terms of water systems.

Some water systems employ a plurality of water treatment agents for which the monitoring of separate target-specie indicators would improve system efficiency. The values of separate target species for the plurality of water treatment agents may be determined by monitoring a plurality of target-specie indicators, each of which may be related to different water treatment agents. In some instances, the system demand and/or system consumption for a plurality of water treatment agents may be related to a single target specie, and the monitoring of a single target-specie indicator may be related to the in-system concentration adjustments for all of the treatment agents. In either instance, such plurality of water treatment agents may be fed to the water system at the same point or at sites along separate streams.

A single water treatment agent may be subject to a plurality conditions accounting for system consumption. In some systems, only one of a plurality of target species for a given water treatment agent is crucial, and only the crucial target specie needs to be monitored. In other systems, a plurality of target species for a given water treatment agent are significant and the determination of system consumption conditions for each target species would improve system efficiency. Moreover, a plurality of system consumption conditions for a single water treatment agent may be determined by quantifying a plurality of target species, each of which may be related to different system consumption conditions for the water treatment agent.

Some water systems may have a plurality of zones in each of which a single water treatment agent may encounter distinct system consumption conditions of different severities. Such zones may be disposed sequentially or in parallel, or the water system may have a plurality of streams that each feeds a portion of the water treatment agent to a zone or carries a portion of the water treatment agent residual away from the zone. The present invention can be employed in any of these situations or combinations of situations, provided that the target-specie indicator(s) is monitored across the water system zone for which a separate treatment-agent consumption is to be determined without any intervening water treatment agent-consumption zones.

The solids and/or solutes within the waters of these water systems may be substantially or mainly organic, or substantially or mainly inorganic, or a mixture of both organic and inorganic materials. The process of the present invention would generally not be applicable to an industrial water system wherein the water system has a high solids loading, for instance a solids loading in excess of 40%.

A water system may contain dissolved solids or dissolved gases, or it may be a slurry (dilute or concentrated), or it may be a slurry containing dissolved solids and/or gases. A water system may also contain liquids other than water, which liquids may be miscible or immiscible with water.

The common target specie of cooling water systems and boiler water systems are mentioned in brief above. Cooling water systems and boiler water systems are preferred water systems for the present invention. They are highly dynamic water systems in great need for the advantages provided by the present invention. The present invention is, however, applicable to a wide variety of industrial water systems as noted above. Some characteristics of several of these water systems are described in more detail below, and such discussion is exemplary, not limiting.

In a cooling water system, the high heat capacity of water makes water a favored heat transfer medium for cooling a product or process, such as those of a wide variety of industries, including the utility industries. The basic cooling system designs are once-through systems, closed recirculating systems (nonevaporative), and open recirculating systems (evaporative). Modern cooling towers recirculate water, and often release heat transferred to its water through evaporation, and thereby reduce the water withdrawn from, and discharged to, natural water sources. While such modern cooling system designs benefit environmental and conservation interests, they spawn water chemistry problems within the cooling system by increasing the potential for corrosion, scaling, fouling and other deposition.

Cooling water usually does not contact the heat source directly. The cooling water and the product/process being cooled are usually both fluids, separated by a barrier that is a good heat conductor, which commonly is a metal or metal alloy. The barrier is called a heat transfer surface, and an assembly of barriers in a containment vessel is called a heat exchanger.

In cooling water systems, and most other industrial water systems, corrosion can cause premature metal failures. Deposits of corrosion products reduce both heat transfer and flow rates and reduce integrity of heat-exchange surfaces and system equipment. Scale is caused by the precipitation of compounds that become insoluble at elevated temperatures, such as calcium carbonate. Scale deposits interfere with heat transfer and reduce flow. Fouling results from the settling out of suspended solids, build up of corrosion products, and growth of microbial masses. Fouling not only interferes with heat transfer and fluid flow, but also promotes severe corrosion under deposits.

In a boiler water system, a boiler is a vessel in which water is vaporized into steam by the application of heat, typically on a continuous basis. The steam generated is most often used either as a direct or indirect heat transfer medium and/or to generate electric power. High pressure and/or high capacity boilers generally are water-tube boilers in which water is circulated within tubes and the applied heat (combustion products such as flame and hot combustion gases) flows across the outside of the tubes. Some of these water tubes may comprise the walls of the furnace in which the heat-generating combustion occurs.

Boiler water systems include the water systems of recovery boilers, used for instance in the pulp and paper industry, power boilers, boilers in the chemical process industry and the nuclear power generation industry which may comprise fluids with a high radioactive contamination level under high pressure.

Limits on boiler cycles of concentration, so as to limit the maximum impurity concentration within a boiler, are routinely set by boiler and turbine manufacturers, water treatment companies and the industrial plants employing the boilers. Boiler feedwater, which normally is comprised of both makeup water and recirculated condensate water, contains some impurities regardless of the extent to which such waters are treated before being fed to a boiler. When steam is generated, substantially pure water vapor is discharged from the boiler, leaving the impurities behind, which increases their concentration in the boiler water. The discharged steam is replaced by contaminant-containing feedwater. An ever increasing concentration of dissolved and suspended solids in the boiler water would inevitably result in very serious problems, including deposit formation, corrosion, foaming and carryover, decreased heat transfer efficiency, boiler tube failure or occlusion, and the like. Boiler-impurities concentration (boiler solids concentration) is offset by withdrawing water as normal blowdown and replacing that blowdown with makeup water containing a lower concentration of dissolved and suspended solids. The heat energy in the normal blowdown, however, is a major factor reducing a boiler's thermal efficiency, and therefore a blowdown rate in excess of that required to limit solids concentration is routinely avoided. An excessive blowdown rate also unnecessarily increases water costs.

Intermediate and high pressure boilers have heat transfer rates in excess of 100,000 Btu/ft$^2$-hr (2,500 cal/m$^2$-hr) and the presence of an even extremely thin deposit layer within the boiler would cause a serious elevation in the temperature of the tube metal. Therefore the feedwater purity is very high and the permitted concentration of impurities introduced with the feedwater is very low. These are generally high cycles value boilers with almost constant steam generation demands.

Both the limitations on boiler concentration cycles and the employment of boiler water treatment programs are intended for, and are generally necessary to, the avoidance of serious scale formation/deposition despite an otherwise adequate feed water purification program.

In a wastewater system, the ultimate fractions produced in a typical waste water system are destined either for recycle to the water system generating the waste, or for recycle to a different system, or for disposal. These "products" of a waste water treatment plant seldom have a value commensurate with that of the water system generating the waste. A typical waste water treatment plant is therefore extremely sensitive to the economics of the treatment agent involved, and unlike the average process plant, its influent is extremely variable and its water treatment agent and other in-system concentration regulating means are far less sensitive than that of a typical process plant. The process of the present invention enables a plant to be proactive in its water treatment agent in-system concentration adjustments, and abnormal target specie value determinations will alert plant operators of inlet water quality upsets. Waste waters and/or systems for purposes of the present invention are most often waters that have been discharged from a prior system or cooling water system or boiler stream.

Raw water streams and/or systems for the purposes of the present invention are waters being prepared for addition to, and use in, a system or cooling water system or boiler stream, and include without limitation well water, river water and other surface water supplies.

The water of typical raw water system can be characterized by the following physical and/or chemical property ranges, although the present invention is not limited to water systems within such ranges:

a pH of from about 2 to about 12;
a temperature of from about 5° C. (41° F.) to about 245° C. (500° F.);
an insoluble solids content of from about 1 ppm to about 1,000 ppm; and
a total solids content of from about 100 ppm to about 100,000 ppm.

In a membrane filtration water system, the use of semipermeable membranes is a comparatively recent addition to the technology of industrial water purification. In membrane separation, influent passes though the membrane as a result of a driving force, or a combination of driving forces, leaving behind some portion of its original impurities as a concentrate. Membrane filtration is a membrane separation process that removes not only suspended particles, but also colloids and solutes from feedwater, as described in more detail below.

The problems that have historically plagued industrial applications of membrane separation include membrane scaling, membrane fouling and membrane degradation. These problems previously kept membrane separation costs relatively high and limited its use to special situations, for instance situations in which the removed impurities themselves were of commercial value. Improvements in membranes and application technology have now made membrane separation a more commercially-practical technology for purifying raw water for industrial water systems, industrial-process effluent treatment, treatment of other waste water, desalination of brackish water, sea water, nonaqueous fluids, mixtures of aqueous and nonaqueous fluids and the like. Membrane separation has also been made more practical for industrial use, particularly industrial use for raw and wastewater purification, by improved tools for determining membrane performance, including detection and/or quantification of membrane fouling, and the dosage and/or performance of membrane-filtration chemicals. Membrane separation would be made still more practical for industrial use by even better diagnostic tools.

Diagnostic monitoring of membrane filtration systems is extremely important to operational efficiency and to avoid foreshortening the useful life of the membrane. These diagnostic monitorings are routinely made in some manner in industrial membrane filtration plants because the diagnostic information provided is now understood and accepted as essential to the system's practicality for industrial use. Monitorings of membrane-filtration chemicals, including without limitation, treatment chemicals that enhance membrane-separation process performance, antiscalants that retard/prevent membrane scale deposition, antifoulants that retard/prevent membrane fouling, biodispersants, microbial-growth inhibiting agents such as biocides and cleaning chemicals that remove membrane deposits, to determine actual system consumption for target species and performances of treatment agents and programs would greatly enhance the operational efficiency of the system and protect the membrane, but the available techniques either so lack sensitivity or take so long that expeditious responsive action is not always possible. Moreover, these pluralities of monitorings routinely require the employment of a plurality of analytical techniques, which situation complicates and increases the expense of the indispensable diagnostic programs.

Many oil, gas and geothermal wells employ extensive water systems in contact with metal surfaces. Such metal surfaces, particularly those disposed downhole, have severe potential water chemistry problems, including without limitation potential corrosion and scaling problems. Water treatment programs employed to resist these problems would be greatly enhanced by a sensitive method for monitoring real-time system consumption of the target species and water treatment agents used therein. The present system is of course not limited to heat-transfer or water-purification water systems or to monitor the system consumption for a downhole corrosion inhibitor or target specie thereof, for instance corrosion products, in the oil and gas well industry. The present invention may be applied to monitor the system consumption for water treatment agents or target specie thereof employed in ore beneficiation water systems, or in chemical refining water systems, or in other industrial water systems.

An important advantage of the present invention is that by monitoring a target-specie indicator, a given embodiment of the invention may be used on a variety of water systems, in a variety of industries, which employ different water treatment agents. Water treatment agents for controlling scaling, corrosion and the like often differ from industry to industry. The embodiments of present invention, not being tied to the treatment agent itself, may be used in dissimilar industries when the target species are the same. There is a greater distribution of the same target specie among the various industries than the employment of the same water treatment agents.

In preferred embodiments, a minimal or specified limit on consumption of at least one water treatment agent and/or target specie is also monitored, more preferably by fluorescence analysis, for instance by using a "traced treatment agent" and/or "traced target specie", such as a treatment agent product or makeup water to which an inert fluorescence tracer has been added in known proportion to the water treatment agent and/or target specie. Monitoring the level of such tracer and target specie and/or water treatment agent within the system determines the minimal or specified limit on consumption concentration of the treatment agent and/or target specie in the system. The concentration of an inert tracer added to the system in proportion to a treatment agent and/or target specie is proportional to the theoretical concentration of the treatment agent and/or target specie in the absence of any treatment-agent and/or target specie selective impacts on concentration. The in-system concentration of an inert tracer can be correlated to the in-system treatment agent and/or target specie concentration under operating conditions associated with minimal or specified limit on (selective) consumption. Most water treatment agents and/or target specie will undergo some type of consumption (system consumption) within the system that is selective to it, that is, by virtue of a mechanism that changes the concentration of the treatment agent and/or target specie but has no substantial impact on the concentration of an inert tracer. Preferably, the inert tracer concentration is reduced by no more than 10%. The actual concentration of a water treatment agent and/or target specie in a water system at any point in time is a function of the amount being added per time unit and the amounts selectively and nonselectively consumed (lost) per time unit.

The concentration of an inert tracer added to the system in proportion to a treatment agent and/or target specie is also a measure of the impact of any adjustments of system controls to regulate the in-system concentration of a treatment agent, particularly when a plurality of adjustments are made concomitantly. For instance, if the goal is a 20 percent decrease in the concentration of the treatment agent then in the system, and the chosen control adjustment is a temporary increase the blowdown from the system with a concomitant fresh water replacement, the inert tracer monitoring will disclose when the goal has been met as to the dilution mechanism, but of course not as to any treatment-agent selective impacts on its concentration during the time interval. The greater the complexity of the nonselective or divergent influences on in-system concentration, the more useful is the use of an inert tracer to track the net effect of these influences. Nonetheless the complimentary monitoring of an inert tracer may be extremely advantageous even when relatively simple control adjustments are made or when quantitative data is not determined. For instance, when the target-specie indicator monitoring indicates that an increase in treatment agent in-system concentration is needed, a monitoring of a tracer in the system may be used to confirm that an upward adjustment of zero, low or consistent consumption in-system concentration of the treatment agent has been made, without quantifying the in-system concentration of the treatment agent before and/or after the adjustment.

A "feed rate" monitoring for the inert tracer of a traced water treatment product or makeup water is at times a preferred additional procedure, for instance by monitoring the tracer's concentration in a feed line upstream of the point at which the product and/or water is delivered to the system. Such "feed rate" monitoring is used to precisely determine the actual amount of treatment agent and/or target specie being added to the system when the tracer is monitored in the feed line. The regulating of the in-system concentration of the present invention might combine at least some of the information provided by the monitoring of a tracer(s) upstream or downstream of the feed inlet to the water system with at least some of the information available concerning the concentration of the tracer(s) in the water treatment agent and/or target specie feed.

The regulation of a water treatment agent in-system concentration may include any of a number of determinations based on monitoring of one or more inert tracers, which values may be relative values, quantitative values, or approximate quantitative values. The proportion between a tracer and the active water treatment agent and/or target specie as fed to a water system need not be known provided the proportion is constant, or instead the proportion can change provided sufficient information is available to correlate the monitorings over the desired time period.

To quantify the fluorescent characteristic of a target-specie indicator, a variety of fluorescence analysis methods are available for use singly or in combination. Such fluorescence analysis techniques include, without limitation, techniques that measure and/or indicate:
1. the appearance or disappearance of fluorescence;
2. a shift in excitation and/or emission wavelengths of fluorescence;
3. a fluorescence quenching (by a specific substance) or elimination of quenching;
4. fluorescence changes based on specific light absorbance changes (increase or decrease);
5. a well-defined temperature-dependency of fluorescence;
6. a well-defined pH-dependency or other water condition dependency of fluorescence; and
7. the exploitation of a temperature-dependency and/or pH-dependency of fluorescence to see or enhance the effects of techniques 1 to 4.

The detection and quantification of specific substances by fluorescence emission spectroscopy are founded upon the proportionality between the amount of emitted light and the amount of a fluorescent substance present. When energy in the form of light, including ultra violet and visible light, is directed into a sample cell, fluorescent substances therein will absorb the energy and then emit that energy as light having a longer wavelength than the absorbed light. A fluorescing molecule absorbs a photon resulting in the promotion of an electron from the ground energy state to an excited state. When the electron's excited state relaxes from a higher energy vibrationally-excited state to the lowest energy vibrationally-excited state, energy is lost in the form of heat. When the electron relaxes to the ground electronic state, light is emitted at a lower energy than that absorbed due to the heat-energy loss, and hence at a longer wavelength than the absorption. The amount of emitted light is determined by a photodetector. In practice, the light is directed into the sample cell through an optical light filter so that the light transmitted is of a known wavelength, which is referred to as the excitation wavelength and generally reported in nanometers ("nm"). The sample cell is designed to optimize the fluorescence response for the analyte, depending on the analysis method chosen. The emitted light is similarly screened through a filter so that the amount of emitted light is measured at a known wavelength or a spectrum of wavelengths, which is referred to as the emission wavelength and generally also reported in nanometers. When the measurement of the fluorescence intensity of specific substances or categories of substances at low concentrations is desired or required, such as often is the case for the process of the present invention, the filters are set for a specific combination of excitation and emission wavelengths, selected for substantially optimum low-level measurements.

In general, the concentration of a target-specie indicator or fluorescent tracer can be determined from a comparison of a sample's emission intensity to a calibration curve of the given target-specie indicator's or tracer's concentration versus emission, for the same set of excitation wavelength/emission wavelengths. Such a concentration-by-comparison method by which the sensed emissions are converted to a concentration equivalent preferably is employed to determine concentrations of a target-specie indicator or tracer that are within the concentration range over which a linear emission response is observed, and this concentration range is referred to herein as the "linear-emission-response concentration range". The linear-emission-response concentration range is to some extent dependent upon the specific target-specie indicator or tracer and the excitation wavelength/emission wavelength set employed. At target-specie indicator or tracer concentrations higher than a given fluorescent target-specie indicator's or tracer's linear-emission-response concentration range, there is a negative deviation from ideal (linear) behavior, the degree of emission for a given concentration being less than predicted by a linear extrapolation. In such instances, the sample can be diluted by known factors until the concentration of the fluorescent target-specie indicator or tracer therein falls within the linear-emission-response concentration range. Two other correction techniques are available when the concentration is higher than the linear-emission-response concentration range. Since the linear-emission-response concentration range is to some extent dependent upon the excitation wavelength/emission wavelength set employed, an alternate excitation wavelength/emission wavelength set could be used. The use of sample cells with shorter pathlengths for the excitation/emission light will also correct or alleviate the problem. If the fluorescent target-specie indicator or tracer is present in the sample at only exceptionally low concentrations, there are techniques for concentrating the target-specie indicator or tracer by known factors until its concentration falls within the linear-emission-response concentration range or is otherwise more readily measured, for instance by liquid-liquid extraction. Nonetheless, preferably a calibration curve over the linear-emission-response concentration range would be prepared or obtained before employing a given target-specie indicator or tracer. Preferably, the target-specie indicator or tracer would be respectively selected or added to the water treatment agent feed in an amount sufficient to provide a concentration of the target-specie indicator or tracer in the sample that is within the linear-emission-response concentration range. Generally, the linear-emission-response concentration range of a fluorescent target-specie indicator or tracer is sufficiently broad to readily determine the amount of the target-specie indicator or tracer that will be sufficient for this purpose. A linear-emission-response concentration range for an unmodified sample and typical standard equipment will most often extend through a concentration range from a concentration of "m" to a concentration of at least 2,000 m. When "extended" operation techniques are employed, for instance sample dilution, use of an optimal alternate excitation wavelength/emission wavelength set, and/or use of optimal small cell pathlengths, a linear-emission-response concentration range can be extended from m to 10,000,000 m and beyond.

A determination of the concentration of a target-specie indicator or tracer in a system can be made when the concentration of the target-specie indicator or tracer in the water system is as low as several parts per million (ppm), or parts per billion (ppb), and at times as low as parts per trillion (ppt). In preferred embodiment, the amount of a fluorescent tracer added to the water treatment agent feed should be sufficient to provide a concentration of the tracer in the water system sample of from about 50 ppt to about 10 ppm. The capability of measuring very low levels is an immense advantage. Such fluorescence analyses (the measurements of the light emitted in response to the light transmitted to the water system sample) can be made on-site, preferably on an almost instant and continuous basis, with simple portable equipment.

As mentioned above, at times it may be desired to monitor a plurality of fluorescent target-specie indicators or tracers. For instance, it may be desired to monitor more than one target specie, or a target-specie indicator and tracer for each of one or more water treatment agents, or distinct target-specie indicators for more than one water treatment agent. In some instances it may be desired to use a plurality of target-specie indicators and/or tracers solely for a single water treatment agent, for instance to confirm that a target-specie indicator or tracer is not undergoing any selective loss. Such separate and distinct target-specie indicators or tracers can all be detected and quantified in a single water system sample despite all being fluorescent substances if their respective wavelengths of emission do not interfere with one another. Thus concurrent analyses for multiple target-specie indicators or tracers are possible by selection of target-specie indicators or tracers having appropriate spectral characteristics. Preferably separate wavelengths of radiation should be used to excite each of the target-specie indicators or tracers, and their fluorescent emissions should be observed and measured at separate emission wavelengths. A separate concentration calibration curve may be prepared or obtained for each target-specie indicator or tracer. In other words, more than one target-specie indicator or tracer can be employed, and then the presence and/or concentration of each such target-specie indicator or tracer in the water system may be determined using analytical parameters (particularly the excitation/emission wavelengths) effective for each such target-specie indicator or tracer, which analytical parameters preferably are sufficiently distinct to differentiate between measurements. Since a plurality of target-specie indicators or tracers may be separately but concomitantly monitored, the present invention does not exclude the use of one or more additional target-specie indicators or tracers for purposes other than the present invention, nor does it exclude the concomitant use of a target-specie indicator or tracer for purposes of the present invention and for some other purpose.

Fluorescence emission spectroscopy on a substantially continuous basis, at least over a given time period, is one of the preferred analytical techniques for the process of the present invention. It is one of the preferred analysis techniques for quantifying and determining the concentration of the target-specie indicator or tracer in a system for regulating water treatment agents and it is an analysis technique having significant advantages.

A dual-monochromator spectrofluorometer can be used for a fluorometric analysis conducted on an intermittent basis and for on-line and/or continuous fluorescence regulating. Portable or compact fluorometers equipped with appropriate excitation and emission filters and quartz flow through cells are commercially available, for instance from Turner Designs (Sunnyvale, Calif.).

In general, for most fluorescence emission spectroscopy methods having a reasonable degree of practicality, it is preferable to perform the analysis without isolating in any manner the target-specie indicator or tracer. Thus there may be some degree of background fluorescence in the water system on which the fluorescence analysis is conducted, which background fluorescence may come from chemical compounds in the water system that are unrelated to the present invention. In instances where the background fluorescence is low, the relative intensities (measured against a standard fluorescent compound at a standard concentration and assigned a relative intensity, for instance a relative intensity of 100) of the fluorescence of the target-specie indicator or tracer versus the background can be very high, for instance a ratio of 100/10 or 100/2 when certain combinations of excitation and emission wavelengths are employed even at low target-specie indicator or tracer concentrations, and such ratios would be representative of relative performance (under like conditions) of respectively 10 and 50. In preferred embodiment, the excitation/emission wavelengths and/or the target-specie indicator or tracer are selected to provide a relative fluorescence of at least about 5 or 10 for the given background fluorescence anticipated.

For instance, for most water system backgrounds, a compound that has a relative performance of at least about 5 at a reasonable concentration is very suitable as a target-specie indicator or tracer. When there is or may be a specific chemical specie of reasonably high fluorescence in the background, the target-specie indicator or tracer and/or the excitation and/or emission wavelengths often can be selected to nullify or at least minimize any interference of the tracer measurement(s) caused by the presence of such specie.

One method for the continuous on-stream monitoring of chemicals by fluorescence emission spectroscopy and other analysis methods is described in U.S. Pat. No. 4,992,380, the disclosure of which is incorporated hereinto by reference.

The combination of high-pressure liquid chromatography ("HPLC") and fluorescence analyses of target-specie indicators or tracers is a powerful tool for the present invention, particularly when very low levels of a target-specie indicator or tracer are used or the background fluorescence encountered would otherwise interfere with the efficacy of the fluorescence analysis. The HPLC-fluorescence analysis method allows a target-specie indicator or tracer compound to be separated from the fluid matrix and then a target-specie indicator or tracer concentration can be measured. The combination of HPLC-fluorescence analysis is particularly effective for measuring minute levels of target-specie indicator or tracer in highly contaminated fluids.

When the target-specie indicator is nonfluorescent and the incipient reagent is fluorescent, a fluorescence analysis technique, such as those described above, will be focused on the fluorescence of the incipient reagent. The measure of the target specie will be the loss of the incipient reagent, as it is consumed in the formation of the target-specie indicator, as manifested by the change of its fluorescence intensity and/or excitation/emission wavelength characteristics. Similarly, if both the target-specie indicator and the incipient reagent are fluorescent, but have different fluorescent characteristics, for instance different wavelengths of maximum emission, the fluorescence analysis technique might focus on the loss of light emitted at the incipient reagent's wavelength of maximum emission, or instead on the increase of light emitted at the target-specie indicator's wavelength of maximum emission, as a function of the formation of the target-specie indicator from the interaction between the incipient reagent and target specie.

Colorimetry, chemiluminescence or spectrophotometry, with or without statistical analysis, may be employed to detect and/or quantify a chemical tracer. Colorimetry is a determination of a chemical specie from its ability to absorb ultraviolet or visible light. One colorimetric analysis technique is a visual comparison of a blank or standard solution (containing a known concentration of the tracer specie) with that of a sample of the fluid being monitored. Another colorimetric method is the spectrophotometric method wherein the ratio of the intensities of the incident and the transmitted beams of light are measured at a specified wavelength by means of a detector such as a photocell or photomultiplier tube. Using a colorimetric probe, a fiber optic (dual) probe, such as a Brinkman PC-80 probe (570 nm filter), a sample solution is admitted to a flowcell in which the probe is immersed. One fiber optic cable shines incident light through the sample liquid onto a mirror inside the cell and reflected light is transmitted back through the sample liquid into a fiber optic cable and then to the colorimetric analyzer unit, which contains a colorimeter, by the other cable. The colorimeter has a transducer that develops an electrical analog signal of the reflected light characteristic of the tracer concentration. The voltage emitted by the transducer activates a dial indicator and a continuous line recorder printout unit. A set point voltage monitor may be employed to constantly sense or monitor the voltage analog generated by the colorimeter, and upon detection of a tracer signal, a responsive signal may be transmitted to a responsive treatment agent feed line to commence or alter the rate of feed. Such a colorimetric analysis technique and the equipment that may be employed therefor are described in U.S. Pat. No. 4,992,380, incorporated hereinto by reference. Chemical tracers suitable for use in conjunction with a colorimetric technique include transition metals and substances which show light absorbance which is detectable from that of other species present in the system fluid or substances which react with color-forming reagents to produce light absorbance which is detectable from that of other species present in the system fluid.

An ion selective electrode may be used to determine the concentration of an inert chemical tracer through the direct potentiometric measurement of specific ionic tracers in aqueous systems. These electrodes respond only to selected ionic materials and gases dissolved in liquids, and hence such tracers must be ionized (or dissolved gases) in the environment in which they are to be determined. Ion selective electrodes work like pH electrodes, depending on a potential developed across a thin membrane by the difference in the concentrations of the ion (or gas) to be measured on each side of the ionically conducting thin layer. The concentration within the electrode is fixed and the potential varies with the concentration of ions (or gas). By calibration (the potential or current versus the concentration), the ionic (or gas) concentration at the sample electrode can be indexed to a reference or standard electrode that is insensitive to the tracer ion. To provide continuous monitoring of the tracer, the electrodes may be dipped directly into a stream of one of the fluids (collectively comprising a flow cell), or the fluid being monitored may be passed through an external flow cell into which the ion-selective and reference electrodes have been inserted. An ion selective electrode tracer monitoring technique and the equipment therefor are described in U.S. Pat. No. 4,992,380, incorporated hereinto by reference.

A transition metal compound (transition metal ions, oxy-anions, cations and associated complexes) can be quantitatively measured by one or more of known techniques. A preferred technique is the colorimetry analysis described above. Another technique is molecular absorption. Molecular absorption in the ultra violet and visible region depends on the electronic structure of the molecule. The energy absorbed elevates electrons from orbitals in a lower-energy state to orbitals in a higher-energy state. A given molecule can absorb only certain frequencies because only certain states are possible in any molecule and the energy difference between any ground and excited state must be equal to the energy added. At a frequency that is absorbed by a molecule, the intensity of the incident energy is greater than the intensity of the emergent energy, and is a measure of the absorbance. A sample of the fluid being monitored may be compared to a calibration curve (absorbance versus concentration) prepared from standard solutions containing known concentrations of the transition metal (or other suitable tracer specie) to detect and determine the concentration of the tracer. A molecular absorption technique for transition metal tracers is described in U.S. Pat. No. 4,992,380, incorporated hereinto by reference.

While fluorescence analysis of an inert fluorescent tracer is a preferred technique when an inert fluorescent tracer is being monitored, as seen from the above descriptions, other methods are available for monitoring other inert tracers, and in broad embodiment the present invention does not exclude the use of other inert tracers and analysis methods suitable therefor. Moreover the present invention in broad embodiment does not exclude the use of such other techniques for monitoring a target-specie indicator, particularly when the target-specie indicator is the target specie itself, particularly when such an alternative method can be conducted without undue interference, and with sufficient rapidity for purposes of determining the system consumption for the target specie.

Analytical techniques for quantifying the presence and/or concentration of a chemical specie without isolation thereof are within an evolving technology, and the above survey of analytical techniques for use in monitoring a target-specie indicator or tracer in the process of the present invention may presently not even be exhaustive, and most likely techniques equivalent to the above for the purposes of the present invention will be developed in the future.

As noted above, in preferred embodiment, the chemical compound(s) selected as the target-specie indicator or tracer should be soluble or dispersible in the water sample or system in which it is formed or to which it is added and should be either stable in the environment thereof for the useful life expected of the target-specie indicator or tracer, or its loss from the water system due to degradation, deposition, complexation, or other phenomena should be predictable and compensative, particularly since it is desired not merely to detect the presence of some amount of the target-specie indicator or tracer, but also to determine the concentration of both so as to correlate such values to a system demand and/or system consumption for the target specie and regulate water treatment agent in-system concentration based thereon. In preferred embodiment, the combination of the chemical compound(s) selected as the target-specie indicator or tracer and the analytical technique selected for determining the presence of such target-specie indicator or tracer, should permit such determination without isolation of the target-specie indicator or tracer, and more preferably should permit such determination on a substantially continuous and/or on-line basis.

Chemical species such as sulfide, calcium, iron, (bi)carbonate, manganese, alkalinity, phosphate, silicates, sulfate, fluoride, magnesium and other scaling and/or deposit forming ions, all of these ions may be a target specie. Their concentration in an industrial water system can serve as a measure of system consumption for an antiscalant or other water treatment agent employed to combat deposition formation. Their selective loss from a water system would generally be a sign of scale deposit formation. These ions possess no fluorescence characteristics. Nonetheless all are susceptible to in-system concentration quantification by fluorescence analysis by reaction/interaction with an incipient reagent to form a target-specie indicator. The value to be correlated with target specie system demand routinely would be the in-system concentration of at least one of such ions or a value equivalent and/or proportional to such concentration. In combination with an inert tracer, the depletion of such an ion from the system's water by scale deposit formation can also be determined, as described elsewhere herein. The present invention is particularly advantageous when the target specie is one or more scaling and deposit forming ions. The present advantages arise not only from the versatility of the invention in providing both treatment-agent and target-specie system consumption information, but also from the gap between the information here provided and that provided by conventional methods.

The incipient reagent of the invention may itself be fluorescent, and may be an adduct or a complex or other interaction or reaction product formed between a plurality of target species, forming a target-specie indicator. The interaction between the target specie and the incipient reagent may increase, decrease or alter the fluorescence characteristics of the incipient reagent. The measurement of the fluorescence of the target-specie indicator formed provides a value that can be correlated to the concentration of the target specie in the water system.

The medium for the formation of the target-specie indicator and/or the fluorescence analysis of the target-specie indicator might be a substantially aqueous medium, a mixed aqueous/nonaqueous medium or substantially nonaqueous medium, although the use of an aqueous medium for the analysis is most often preferred for the present invention if an aqueous medium will suffice. Suitable techniques for the conversion of a water system sample to other than a substantially aqueous sample are known in the chemical analytical field and include conventional techniques such as liquid/liquid extraction, nonaqueous solvent addition, adsorption onto solids, and others.

The medium for the formation of the target-specie indicator and/or the fluorescence analysis of the target-specie indicator might contain one or more chemical species that enhance or promote the formation of the target-specie indicator and/or the fluorescence analysis of the target-specie indicator.

Some of the fluorescence analysis techniques utilize responses to pH, temperature or other conditions of the medium in which the target-specie indicator is undergoing fluorescence analysis. For instance, a given fluorescence technique measures an alteration in the fluorescence of a sample upon the formation of a given target-specie indicator. The fluorescence alteration may be observed at a particular pH or temperature to which the target-specie indicator medium would be adjusted. The fluorescence alteration might be the appearance or disappearance of fluorescence at a given pH or temperature, a shift in excitation and/or emission wavelengths of fluorescence at a given pH or temperature, a quenching of fluorescence at a given pH or temperature range or light-absorbance dependent changes of fluorescence at a given pH or temperature range.

The addition of an incipient reagent to the water system itself is generally impractical and unnecessary. A side-stream water sample is taken from the water system routinely, and thus the amount of incipient reagent used is minimized. Seldom would it be desirable to contaminate the entirety of a water system with a substance that is normally foreign thereto. The present invention does not, however, exclude the use of an incipient reagent, or a precursor thereto, present in the water system itself, particularly when such approach is practical and/or necessary.

Techniques from various literature sources that can be adapted for the present purposes of formation of the target-specie indicator and/or the fluorescence analysis of the target-specie indicator, when the target specie is a chemical target-specie, are set forth below as exemplitive and are not intended as limiting.

The sulfide anion ($S^{-2}$) is susceptible to quantification by fluorescence analysis and/or fluorometric flow-injection techniques, for instance as described in "Trace Determination of Aqueous Sulfite, Sulfide and Methanethiol by Fluorometric Flow Injection Analysis", P. K. Dasgupta and H. C. Yang, Anal. Chem. 1986, 58(13), p. 2839–2844, incorporated hereinto by reference. The fluorescence analysis is based on the reaction of sulfide with an organic incipient reagent, such as N-acridinylmaleimide, in a water/DMF medium to form a fluorescent product, which fluorescent product has fluorescence characteristics distinguishable from similar reaction products of such organic specie with other sulfur anions, such as the sulfite and methanethiol.

A fluorometer can be used for fluorescence analysis of the aluminum cation in water systems such as cooling water systems.

A fluorometric method for determining microamounts of magnesium cation is based on its reaction with 2-quinizarin sulfonate incipient reagent to form 1:1 and 1:2 metal-to-ligand complexes which, in an ethanol/water medium at a pH of about 10, can be quantified fluorometrically using for instance excitation at 545 nm and measuring the emission intensity at 610 nm, as described in "Determination of Magnesium by Spectrofluorometry and Synchronous Scanning First and Second Derivative Spectro-Fluorometry with 2-Quinizarin Sulfonate", F. Salinas, A. M. De la Pena and F. M. De la Pena, Mikrochim. Acta, 1986, 3(5–6), p. 361–368, incorporated hereinto by reference. Synchronous scanned first and second derivative fluorometry can be used to further increase the sensitivity of the method for low levels of magnesium. Linearity between the fluorescence intensity versus concentration was seen for solutions strengths of from 20 to 200 nanograms ("ng") $Mg^+$/ml (about 20 to 200 ppb), and for solutions strengths of from 10 to 100 ng $Mg^+$/ml (about 10 to 100 ppb) when the first and second derivative approach was used.

For the fluorescence analysis of calcium cations, a calcein disodium salt or fluorexon can be used as complexing reagents, for instance as described in "Use of the Indicator Calcein Disodium Salt Instead of Fluorexon in Complexometric Titration of Calcium Oxide", N. A. Koxhcheeva and L. A. Fartushnaya, Zavod. Lab., 1986, 52(6), p. 90–91, incorporated hereinto by reference. A fluorescent solution can be prepared by combining a dilute HCl solution of calcein disodium salt with 0.2% thymolphthalein in 5% KOH and used for the determination of calcium concentrations.

Another incipient reagent for the fluorescent determination of calcium and other divalent metal ion concentrations is (N-(4-nitrobenzofurazan)monoaza-18-crown-6), a crown ether based fluorophoric reagent, which for example is described in "A New Metal Sensitive Fluorescence Reagent", K. W. Street, Jr. and S. A. Krause, Anal. Lett., 1986, 19(7–8), p. 735–745, incorporated hereinto by reference. Metal cation complexes with this reagent display enhanced fluorescence emissions. The performance of the reagent is sensitive to the solvent system employed, and nonaqueous media provide the most favorable conditions with respect to both sensitivity and complexing ability, although the use of a nonaqueous medium for the analysis is most often undesirable for the present invention if an aqueous medium will suffice. Although the ligand possesses intrinsic acid/base sensitive fluorescence and spectroscopic properties, the metal sensitivity is not attributed to protonation-deprotonation chemistries as is the case for many of the currently available chromogenic and fluorogenic crown reagents. The sensitivity of the reagent is influenced by the anion associated with the metal and the water content of the solvent matrix. The reagent has been used to determine calcium cation concentrations in the range of $(1.5$ to $1.9) \times 10^{-6}$ M. The detection limit for calcium in $H_3C\text{-}CN$ is about 126 ppb.

Preferable incipient reagents for which literature sources describe methods of fluorescence analysis of analytes relevant to the present invention are set forth below in Table 1.

TABLE 1

| Analyte | Fluorescent Reagent | Reference* |
|---|---|---|
| calcium | calcein, a.k.a. fluorescein iminodiacetic acid, or calcein W (water-soluble disodium salt) | 3, page 1741 and 1775 |
| calcium | 1,5-bis(dicarboxymethylaminomethyl)-2,6-dihydroxynaphthalene | 3, page 1747 and 1774 |
| calcium | 3-hydroxy-2-naphthoic acid | 3, page 1775 |
| calcium | isocein, a.k.a. 8-(bis(carboxymethyl)aminomethyl)-7-hydroxy-2-methyl-isoflavone | 3, page 1775 |
| calcium | 8-quinolylhydrazone | 3, page 1777 |
| magnesium | o,o'-dihydroxyazobenzene | 3, page 1931 |
| magnesium | 2,3-bis(salicylideneamino)benzofuran | 3, page 1943 and 1961 |
| magnesium | calcein | 3, page 1953-4 |
| magnesium | 2,2'-dihydroxyazobenzene | 3, page 1955 |
| magnesium | 3-hydroxy-3',4'-dimethylflavone | 3, page 1956 |
| magnesium | 3,3',4'-trihydroxyflavone | 3, p |
| magnesium | 3-hydroxy-2-naphthoic acid | 3, page 1956 |
| magnesium | 8-hydroxyquinoline-5-sulfonic acid | 3, page 1956-7 |
| magnesium | lumomagneson, a.k.a. 5-(5-chloro-2-hydroxy-3-sulfophenylazo)barbituric acid | 3, page 1957 |
| magnesium | morin | 3, page 1959 |
| magnesium | 2,3-bis(salicylideneamino)benzofuran | |
| iron | 1,10-phenanthroline and tetrabromo-, tetraiodo-dichlorotetraiodo-fluorescein | 2, page 745-6 |
| iron (ferric) | pontachrome blue black R (a.k.a.. mordant black 17) complex with ammonium | 2, page 817 |
| iron | 4,4'bis(bis(carboxymethyl)amino)stibine-2,2'-disulfonic acid/hydrogen peroxide | 2, page 853 |
| iron | 4'-(4-methoxyphenyl)-2,2':6',6''-terpyridyl or sulfonate thereof | 2, page 853 |
| copper (cupric ion) | lumocupferron, a.k.a. a-(4-dimethylaminobenzylidene) hippuric acid | 2, page 214 |
| copper (cuprous) | ternary complex of 1,10-phenanthroline and rose bengal | 2, page 230 |
| copper (cupric and cuprous) | thiamine | 2, page 238 |
| copper (cupric) | 1,1,3-tricyano-2-amino-1-propene | 2, page 241 |
| copper (cupric) | 2-hydroxy-1-naphthaldehyde/4-chlorobenzylediethiocarbamate in DMF | 2, page 256 |
| copper (cupric) | 1-(2-hydroxypropyl)anabasine/hydrogen peroxide reaction product | 2, page 257 |
| copper | 1,10-phenanthroline and tetrabromo-, tetraiodo- or dichlorotetraiodo-fluorescein | 2, page 262-3 |
| chloride | N-(sulfopropyl)acridinium | 1, page 145 |
| chloride | N-(6-methoxyquinolyl)acetic acid | 1, page 145 |

TABLE 1-continued

| Analyte | Fluorescent Reagent | Reference* |
| --- | --- | --- |
| chloride | N-(6-methoxyquinolyl)acetoethyl ester | 1, page 145 |

*References corresponding to the numbers listed in Table 1 and incorporated hereinto by reference are: (1) "Molecular Probes - Handbook of Fluorescent Probes & Research Chemicals", 5th Ed., R. P. Haugland, 1992; (2) "Photometric and Fluorometric Methods of Analysis", Part 2, F. D. Snell, 1978 (3) "Photometric and Fluorometric Methods of Analysis", Part 2, F. D. Snell, 1978.

Techniques that can be used for the present purposes of formation of the target-specie indicator and/or the fluorescence analysis of the target-specie indicator, when the target specie is a water condition, are set forth below as exemplitive and not limiting. The acid/base sensitivity of the fluorescence characteristics of a incipient reagent may be employed to determine the pH of a water system. Suitable incipient reagents are reagents whose fluorescence intensity increases or decreases, or whose excitation and/or emission wavelength(s) shifts, upon reaction with, or in the presence of, the target specie. Examples of suitable incipient reagents for pH determinations include acridine orange, acridine yellow, acriflavine, 4-aminobenzoic acid, 4-aminobiphenyl, fluorescein, and many others.

By the terms "tracing" is meant herein, unless expressly indicated otherwise, the determination of the concentration of an inert tracer(s) in a water aqueous system. Such tracing could be conducted on a singular, intermittent or semi-continuous basis for the purpose of the present invention, but preferably on a substantially continuous basis, and, more preferably, the concentration determination is conducted on-site (at the site of the water system). Inert tracers are at times referred to herein simply as a "tracer".

Generally the dosage of a tracer to a water treatment agent feed or makeup water will be at least sufficient to provide a concentration of tracer at the downstream sampling/monitoring station of at least about 50 ppt (parts per trillion), and more commonly at least about 5 ppb (parts per billion) or higher, up to about 100 or 1,000 ppm (parts per million), in the water system.

A water treatment agent feed is commonly, but not always, comprised of one or more active water treatment agents and one or more inert diluents. A diluent is frequently a solvent for the water treatment agent(s), and such solvent can be, and in many instances is, water. A diluent is frequently included in the water treatment agent feed to facilitate the rapid and substantially homogeneous distribution of the active water treatment agent(s) in the water system to which the water treatment agent feed is charged. The concentration of the active water treatment agent(s) in the water treatment agent feed is generally from about 0.5 to about 50 weight percent and at times higher. The weight ratio of active water treatment agent(s) to tracer in the water treatment agent feed is often within the range of from about 10:1 to about 1,000. The weight ratio between the active water treatment agent and the tracer in a system ahead of any selective water treatment agent-consuming site is of course substantially the same as that of the water treatment agent feed, and thereafter that weight ratio would fall as the water treatment agent is selectively consumed in the water system, for instance to the extent of approaching a 1:1 weight ratio or less. A selective release of water treatment agent, which is also a factor in its system consumption, would of course have the opposite effect on this ratio.

The tracer is preferably selected from among those that are easily quantifiable by a fluorescence analysis method, a preferred analytical technique for the purposes of the present system. Other analysis methods not excluded for use in quantifying the tracer are described elsewhere herein.

An inert tracer preferably is both soluble and stable in the water treatment agent feed and. transportable with the water of the water system and thus wholly water-soluble therein at the concentration it is used, under the temperature and pressure conditions to be encountered. Preferably the selected inert tracer also meets the following criteria:

1. Be thermally stable and not decompose at the temperature within the given system;
2. Be detectable on a continuous or semicontinuous basis and susceptible to concentration measurements that are accurate, repeatable and capable of being performed on system water;
3. Be substantially foreign to the chemical species that are normally present in the water of the water systems in which the inert tracer may be used;
4. Be substantially impervious to interference from, or biasing by, the chemical species that are normally present in the water of the water systems in which the inert tracer may be used;
5. Be substantially impervious to any of its own potential specific losses from the water of the water system, including selective carry-over;
6. Be compatible with all treatment agents employed in the water of the water systems in which the inert tracer may be used, and thus in no way reduce the efficacy thereof;
7. Be compatible with all components of the water treatment agent feed formulation or makeup water despite the concentrations of the tracer and/or other components in such a formulation, and despite any storage and/or transportation conditions encountered; and
8. Be reasonably nontoxic and environmentally safe, not only within the environs of the water of the water system in which it may be used, but also upon discharge therefrom.

The chemical compound(s) selected as an inert tracer(s) should not be one that is consumed or selectively lost to the water of the water system, for instance due to degradation, deposition, complexation, or other phenomena, unless such loss is at a rate that is predictable and proportional to a non-system-consumption loss of the water treatment agent or target-specie indicator being monitored. An inert tracer(s) used in the present invention is preferably substantially unconsumed in the water system environment. An inert tracer(s) that is wholly inert in the water system environment would not react to a substantial degree with any of the components in the water of the water system to which it is added, would not degrade in the environment of the water of the water system, would be incapable of coupling and/or depositing in any manner within such system and would not appreciably be effected by other system parameters such as metallurgical composition, heat changes or heat content. There are water-soluble inert tracer(s) that are wholly inert, or substantially inert, in the aqueous environments likely to be encountered in industrial water systems. Further, it is believed that an inert tracer(s) having a degree of inertness such that no more than 10 weight percent thereof is lost due to reaction, degradation, coupling and/or deposition during the time that elapses between its addition and its final analysis, is sufficiently, or substantially, inert for the purpose of the present invention for most, if not all, target-specie indicator and/or water treatment agent monitorings.

As noted above, an inert tracer must be added to the makeup water and/or water treatment agent feed in known proportion to the target specie and/or water treatment agent, and preferably an inert tracer is introduced into the water system together with the target specie and/or water treatment agent at a known and constant concentration therein which is at a known and constant proportion to the target specie and/or water treatment agent therein. The preferred method of achieving such proportionality is to formulate an inert tracer together with water treatment agent concentrate if the water treatment agent feed is to be prepared by on-site dilution and if an inert tracer is stable in such concentrate. The concentrate may be an aqueous solution or other substantially homogeneous admixture that disperses with reasonable rapidity in the dilution fluid which is added. Since in most any instance a water treatment agent and an inert tracer would both be added to a system as components of a fluid feed formulation, rather than as a dry solid or individual neat liquids, the tracer concentration may be correlated not to the numerical concentration of an inert tracer itself or the water treatment agent itself, but instead to the concentration of a formulated product containing the water treatment agent, which in turn can be correlated to the concentration of an inert tracer and/or water treatment agent when and if such information is required. Therefore the proportionality of the tracer to the water treatment agent feed for the purposes of the present invention can be equivalent to a proportionality of tracer to the active water treatment agent component of the feed.

Among the substantially water-system inert fluorescent compounds are the mono-, di- and trisulfonated naphthalenes, including their water-soluble salts, particularly the various naphthalene mono-, di-, and tri-sulfonic acid isomers, which are preferred inert tracers for use in the present invention. The naphthalene mono- di- and tri-sulfonic acid isomers are water-soluble, generally available commercially and easily detectable and quantifiable by known fluorescence analysis techniques. Preferred naphthalene mono- and disulfonic acid isomers are the water-soluble salts of naphthalene sulfonic acid ("NSA"), such as 1-NSA and 2-NSA, and naphthalene disulfonic acid ("NDSA" or "NDA"), for instance 1,2-NDSA, 1,3-NDSA, 1,4-NDSA, 1,5-NDSA, 1,6-NDSA, 1,7-NDSA, 1,8-NDSA, 2,3-NDSA, 2,4-NDSA and so forth. Many of these inert tracer(s) (mono-, di- and trisulfonated naphthalenes and mixtures thereof) are extremely compatible with the environments of most systems. Among these preferred fluorescent tracers, 2-NSA and 1,5-NDSA have been found to be thermally stable (substantially inert) at temperatures up to at least about 540° C. (1004° F.), for at least 24 hours at 285° C. (545° F.) and at pressures up to about 1,500 psig for time periods at least commensurate with, and often well in excess of, commercial water system holding times. Such inert fluorescent tracers are not volatilized into steam. Another group of inert fluorescent tracers that are preferred for use in the process of the present invention are the various sulfonated derivatives of pyrene, such as 1,3,6,8-pyrene tetrasulfonic acid, and the various water-soluble salts of such sulfonated pyrene derivatives.

In preferred embodiment an inert tracer is one of the above sulfonated fluorescent tracers and is employed at concentration levels of from about 0.5 ppb, and more commonly at least about 5 ppb or higher, up to about 10 ppm in the water system. Fluorescent chemical tracers and monitoring techniques are now known, for instance as disclosed in U.S. Pat. No. 4,783,314, incorporated herein by reference, wherein fluorescent tracers are employed in combination with a fluorescence monitoring, such as the sodium salt of 2-naphthalenesulfonic acid.

When the tracer is 2-NSA, one of the water-soluble salts of naphthalene sulfonic acid ("NSA"), its concentration in the water system can be fluorometrically measured by excitation at 277 nm and emission measurement at 334 nm, and the emissions observed referenced to a standard aqueous solution containing 0.5 ppm 2-NSA, as acid actives.

Although the tracer used in the present invention is generally an inert tracer, a tracer that is an active treatment agent in one system may be a substantially inert tracer in another system. An active tracer may be, for instance, a corrosion inhibitor. One series of compounds applied to reduce copper and copper-alloy corrosion are aromatic organic corrosion inhibitors. This series of organic compounds, which includes benzotriazole ("BT"), butylbenzotriazole ("BBT"), and tolyltriazole ("IT") and related compounds, react with the metal surface and form protective films on copper and copper alloys. These compounds are active corrosion inhibition treatment components and are referred to generally herein as copper corrosion inhibitors or corrosion inhibitors, or as aromatic azoles, and at times as triazoles or aromatic (tri)azoles. The preferred analytical technique for aromatic (tri)azoles when used as an active tracer in the process of the present invention is fluorescence emission spectroscopy.

Some water systems have no copper, copper alloy or other metal surfaces that require protection from a corrosion inhibitor, and for such systems the use of copper corrosion inhibitors as inert tracers for the purposes of the present invention would generally not be a common embodiment of the invention. The use of copper corrosion inhibitors may nonetheless be a preferred embodiment in such systems when they are already contained in waters that will make up at least a portion of the water treatment agent feed stream or when water from the system will be recycled to a system that needs such corrosion inhibitor. For instance, some industries may recycle water from one water system, such as a cooling tower, through another water system. In such instances, if these copper corrosion inhibitors were added to the water of the first water system for corrosion inhibition and/or active tracer performance, they may be present in the water treatment agent feed and/or makeup water stream of the second water system in sufficient concentration for the purposes of the present invention. Further, if the second water system contains no metal surfaces which lead to consumption of such copper corrosion inhibitors, or at least no such metal surfaces upstream of relevant monitorings, such normally "active" tracers are inert tracers for the purposes of the present invention. For example, if the relevant monitorings were of the water treatment agent feed stream (to determine the feed concentration of the tracer) and a site along the body of the water system, and there were no metal surfaces leading to consumption between these points, the copper corrosion inhibitors would be inert tracers.

The use of other nonpreferred tracers may similarly become a preferred embodiment of the present invention when they are already contained in waters that will make up at least a portion of the water treatment agent feed stream or when the tracer-containing effluent water will be recycled to a system that employs such tracer as a tracer or for other purposes, such as treatment purposes. Certain fluorescent compounds change their fluorescence intensity as measured at a given emission wavelength in response to one or more conditions of the in-system environment, which may be an in-system environmental condition. The present invention does not exclude inert tracer monitoring techniques that comprise or include a change in fluorescence intensity, which is a technique of fluorescence emission spectroscopy as that terminology is used herein.

As used herein, system consumption is a selective change in the concentration of a substance in a system, and is commonly but not necessarily a loss of the substance from a system. The selective loss of scaling ions due to deposit formation is a system consumption for scaling ions. The loss of scaling ions is considered a system consumption factor, which is given positive mathematical sign and represents an increase in the net system consumption for scaling ion. The release of scaling ions which results in a net increase of scaling ions in the system is a system consumption factor, which is given a negative mathematical sign and represents a decrease in the system consumption for scaling ions. The formation of corrosion products, such as $Fe^{+2}$ and $Fe^{+3}$, may be considered a negative system consumption for corrosion products. Since a system consumption for a target specie is a selective change in its concentration in the system, that is, a concentration change not reflected in the in-system concentration of an inert tracer, an appropriate response to a change in system consumption is dependent upon the probable mechanism for the system consumption. If an increase in system consumption for scaling ions is possibly scale formation, an increase in antiscalants may be an appropriate response, and the success of the response will be reflected in a decrease of system consumption as the deposits dissolve or deposit formation stops. In other systems, the precipitation, flocculation, formation of particulates containing scaling ions may be desired, and if the consumption for the target specie is not sufficiently high, an appropriate response may be the addition of treatment agents promoting precipitation, flocculation, or particulate formation formation. Thus despite the correlation between consumptive interaction between a water treatment agent and its target specie, an increase in the system demand for a target specie does not automatically call for an increase in the treatment agent concentration.

Unless expressly indicated otherwise herein, the inclusion of a prefix or suffix in parenthesis designates the word with such prefix or suffix as an alternative. For instance, "specie(s)" means "specie and/or species", "determination(s)" means "determination and/or determinations", "technique(s)" means "technique and/or techniques", "chemical(s)" means "chemical and/or chemicals", "component(s)" means "component and/or components", "tracer(s)" means "tracer and/or tracers", and the like. By "ppm" is meant "parts per million" by weight. By "ppb" is meant "parts per billion" by weight. By "ppt" is meant "parts per trillion" by weight.

The present invention is applicable to industries employing water treatment agents for the treatment of aqueous systems, mixed aqueous/nonaqueous systems and substantially nonaqueous system, including industries employing boiler water systems, cooling water systems, and so forth.

EXAMPLES

Unless indicated otherwise, the water employed to prepare the synthetic industrial water solutions in the following Examples 1 to 5 had the following initial chemistry, which is prototypical of, for instance, industrial cooling waters and is thus referred to herein as "synthetic industrial water":

200 ppm $Ca^{+2}$ (as $CaCO_3$)
200 ppm $Mg^{+2}$ (as $CaCO_3$)
200 ppm $HCO_3^-$ (as $CaCO_3$)
140 ppm $Cl^-$ (as Cl)
194 ppm $SO_4^{-2}$ (as $SO_4$)
90 ppm $Na^+$ (as Na)
pH 8.4

EXAMPLE 1

To demonstrate the application of the present process to an orthophosphate ($PO_4^{-3}$) target specie, the fluorescence analysis of a series of synthetic industrial water solutions, also containing from 0 to 10.0 ppm $PO_4^{-3}$ (as $PO_4$), in the presence of an incipient reagent were conducted and percent relative fluorescence of the target-specie concentration indicators in each solution were determined in comparison to such a solution without that target specie. The incipient reagent was 1-pyrenesulfonic acid in a highly acidic vanadomolybdate aqueous solution. This solution (fluorescent reagent) contains 1.0 ppm 1-pyrenesulfonic acid, (ppm, as acid actives), 2.35 wt./vol. percent ammonium molybdate, 0.125 wt./vol. percent ammonium metavanadate, and 33 vol./vol. percent concentrated hydrochloric acid. The fluorescent reagent (10 ml.) was admixed with 100 ml. of each of the orthophosphate-containing solutions. The fluorescence analysis was conducted after one minute using a Gilford Fluoro IV dual monochromator, with a 1.0 cm×1.0 cm cuvette. An excitation wavelength of 380 nm and an emission wavelength of 405 nm were used. The solution containing the fluorescent reagent but not the orthophosphate was assigned a percent relative fluorescence of 100. The change in the fluorescence characteristic of the incipient reagent when it interacted with the orthophosphate was a decrease in fluorescence intensity under these conditions. The fluorescence characteristic that can be correlated to the target-specie concentration is the emission intensity decrease as the analyte ($PO_4^{-3}$) concentration increases. The fluorescence being measured is affected by that of the complex between incipient reagent and target-specie. The concentration of $PO_4^{-3}$ versus the percent relative fluorescence determined for each sample are set forth in Table 2 below. Such data exhibits a coefficient of linear correlation (r) of 0.98. Perfect linearity would exhibit an r of 1.000.

TABLE 2

| $PO_4^{-3}$ Concentration (ppm as $PO_4$) | Percent Relative Fluorescence |
| --- | --- |
| 0.0 ppm | 100% |
| 2.5 ppm | 72.6% |
| 5.0 ppm | 55.4% |
| 10.0 ppm | 29.7% |

EXAMPLE 2

To demonstrate the application of the present process to a ferrous ion ($Fe^{+2}$) target specie, the fluorescence analysis of a series of synthetic industrial water solutions, also containing from 0.0 to 1.0 ppm $Fe^{+2}$ (as Fe), in the presence of an incipient reagent were conducted and percent relative fluorescence of the target-specie concentration indicators in each solution were determined in comparison to such a solution without that target specie. The incipient reagent was 1,10-phenanthroline, employed in this Example 2 in aqueous solution. This solution (fluorescent reagent) was prepared by adding 1,10-phenanthroline to distilled (DI) water to form a solution containing 1,000 ppm of 1,10-phenanthroline. The fluorescent reagent (1.0 ml.) was admixed with 100 ml. of each of the target-specie-containing solutions, and the fluorescence analysis was conducted after one minute using a Gilford Fluoro IV dual monochromator, with a 0.2 cm diameter cuvette (flowcell). An excitation wavelength of 293 nm and an emission wavelength of 360 nm were used. The solution containing the fluorescent reagent but not the target specie was assigned a percent relative fluorescence of 100. The change in the fluorescence characteristic of the incipient reagent when it interacted with the target specie was a decrease in fluorescence intensity under these conditions. The fluorescence characteristic that can be correlated to the target-specie concentration is the emission intensity decrease as the analyte ($Fe^{+2}$) concentration increases. The concentration of $Fe+2$ versus the percent relative fluorescence determined for each sample are set forth in Table 3 below. Such data exhibits a coefficient of linear correlation (r) of 0.9999.

TABLE 3

| $Fe^{+2}$ Concentration (ppm, as Fe) | Percent Relative Fluorescence |
| --- | --- |
| 0.0 ppm | 100% |
| 0.25 ppm | 79.1% |
| 0.50 ppm | 59.9% |
| 0.75 ppm | 39.0% |
| 1.0 ppm | 19.4% |

EXAMPLE 3

To demonstrate the application of the present process to a cupric ion ($Cu^{+2}$) target specie, the fluorescence analysis of a series of synthetic industrial water solutions, also containing from 0.0 to 2.0 ppm $Cu^{+2}$ (as Cu), in the presence of an incipient reagent were conducted and percent relative fluorescence of the target-specie concentration indicators in each solution were determined in comparison to such a solution without that target specie. The incipient reagent was bicinchoninate (which is also known as 2, 2'-biquinoline-4,4'-dicarboxylic acid, dipotassium salt), employed in this Example 3 in aqueous solution. The solution (fluorescent reagent) of bicinchoninate was prepared by adding bicinchoninate to DI water to form a solution containing 1,000 ppm bicinchoninate. For samples containing 0 to 0.5 ppm $Cu^{+2}$, the fluorescent reagent (0.2 ml) was admixed with 100 ml of each of the target-specie-containing solutions, and the fluorescence analysis was conducted after one minute using a Gilford Fluoro IV dual monochromator, with a 0.2 cm diameter cuvette (flowcell). An excitation wavelength of 260 nm and an emission wavelength of 410 nm were used. For samples containing 0.5 to 2.0 ppm $Cu^{+2}$, the fluorescent reagent (0.6 ml) was admixed with 100 ml of each of the target-species-containing solution, and the fluorescence analysis was conducted after one minute development time as before. The synthetic industrial water solution containing the fluorescent reagent but not the target specie was assigned a percent relative fluorescence of 100. The change in the fluorescence characteristic of the incipient reagent when it interacted with the target specie was a decrease in fluorescence intensity under these conditions. The fluorescence characteristic that can be correlated to the target-specie concentration is the emission intensity decrease as the analyte ($Cu^{+2}$) concentration increases. The concentration of $Cu^{+2}$ versus the percent relative fluorescence determined for each sample are set forth in Table 4 below. Such data exhibits a coefficient of linear correlation (r) of 0.994.

TABLE 4

| $Ce^{+2}$ Concentration (ppm, as Cu) | Percent Relative Fluorescence |
| --- | --- |
| 0.0 ppm | 100% |
| 0.05 ppm | 94.3% |
| 0.10 ppm | 90.0% |
| 0.25 ppm | 65.8% |
| 0.5 ppm | 42.1% |

Additional tests were conducted to determine the compatibility of bicinchoninate with industrial water conditions and chemistries other than those already demonstrated by the use of synthetic industrial water in Example 3 above. The conditions/chemistries tested and the effect thereof on bicinchoninate in aqueous solution is set forth below in Table 5.

TABLE 5

| Water Condition or Chemistry | Effect on Bicinchoninate |
| --- | --- |
| pH from 6 to 13 | no effect |
| highly acidic pH | tends to precipitate |
| 5 ppm $Fe^{+2}$ | no effect |
| 10 ppm $Zn^{+2}$ | no effect |

EXAMPLE 4

To demonstrate the application of the present invention to Total Alkalinity as a target species, the fluorescence analysis of a synthetic industrial water was conducted and percent relative fluorescence of the Target Species concentration indicators in each solution were determined in comparison to such a solution without that Target Species. The incipient fluorescent reagent was 1,000 ppm 4-aminobenzoic acid aqueous solution. The fluorescent reagent (0.1 ml) solution was added to 100 ml of each of the target-species-containing solutions. The fluorescence analysis was conducted with a Gilford Fluoro IV dual monochromator, with 0.2 cm diameter cuvette (flow cell). An excitation wavelength of 275 nm and an emission wavelength of 340 nm were used. The solution containing the fluorescent reagent but 0 ppm (bi)carbonate alkalinity was assigned a percent relative fluorescence of 0% and solution containing fluorescent reagent between pH 6.4–8.9 (without any sulfuric acid neutralizing agent present) was assigned a percent relative fluorescence of 100%. The change in fluorescence character of the incipient reagent was measured after one minute and as it reacted with the total alkalinity was an increase in fluorescence intensity under these conditions. The fluorescence character that can be correlated to the Target Species concentration is the emission intensity increase as the analyte increases. The concentration of Total Alkalinity versus the percent relative fluorescence was determined for each sample and is set forth in Table 6 below.

TABLE 6

| Total Alkalinity Added (as $CaCO_3$) | % Relative Fluorescence |
|---|---|
| 200 ppm (initial) | 4.0% |
| 250 ppm | 8.6% |
| 275 ppm | 14.7% |
| 300 ppm | 85.8% |
| 325 ppm | 91.6% |

EXAMPLE 5

To demonstrate the application of the present process to a (hydrogen) sulfide target specie, the fluorescent analysis of a series of synthetic industrial water solutions also containing 0.0 to 2.24 ppm (hydrogen) sulfide, in the presence of an incipient reagent were conducted and percent relative fluorescence of the target-specie concentration indicators in each solution were determined in comparison to such a solution without that target specie. The incipient reagent was N,N-dimethyl-p-phenylenediamine solution (1,700 ppm in 8M aqueous sulfuric acid). For samples containing 0 ppm to 0.56 ppm (hydrogen) sulfide, the fluorescent reagent (1.0 ml) was admixed with 25 ml of each of the target-specie-containing solutions and then 1.0 ml of aqueous potassium dichromate (1600 ppm as $H_2Cr_3O_7$) was admixed with the fluorescent reagent + target-specie-containing solution. The fluorescence analysis was conducted after five minutes development time using a Gilford fluoro IV dual monochromator, with a 0.2 cm diameter cuvette (flowcell). An excitation wavelength of 660 mn and an emission wavelength of 680 mn were used.

For samples containing 0.56 to 2.24 ppm (hydrogen) sulfide, the same procedure was used, except that fluorescence analysis was conducted at an excitation wavelength of 690 mn and an emission wavelength of 710 mn. The synthetic, industrial water solution containing the fluorescent reagent, chromate and highest level of target specie (for each group of analysis) was assigned a percent relative fluorescence of 100. The change in the fluorescence characteristic of the incipient reagent when it interacted with the target specie was a change in excitation and emission wavelengths and corresponding increase in fluorescence intensity under the stated analysis conditions the concentration of (hydrogen) sulfide versus the percent relative florescence determined for each sample are set forth in Tables 7 and 8 below. Such data exhibits a coefficient of linear correlation (r) of 0.999 for (hydrogen) sulfide concentration at or below 0.56 ppm and r=0.991 for (hydrogen) sulfide concentration from above 0.56 to 2.24 ppm.

TABLE 7

| (Hydrogen) Sulfide Concentration | Percent Relative Fluorescence |
|---|---|
| 0.00 ppm | 0.0% |
| 0.11 ppm | 21.2% |
| 0.28 ppm | 53.3% |

TABLE 7-continued

| (Hydrogen) Sulfide Concentration | Percent Relative Fluorescence |
|---|---|
| 0.56 ppm | 100.0% |

TABLE 8

| (Hydrogen) Sulfide Concentration | Percent Relative Florescence |
|---|---|
| 0.00 ppm | 0.0% |
| 1.12 ppm | 61.9% |
| 1.68 ppm | 82.2% |
| 2.24 ppm | 100.0% |

EXAMPLE 6 -

The Hardness Ion Calcium

A method for the detection of calcium was developed using the reagent 1,2-bis(o-aminophenoxy)ethane-N,N,N', N'-tetraacetic acid (BAPTA). A $5 \times 10^{-3}$ M BAPTA reagent was prepared by dissolving 314 mg of $K_4$BAPTA in 100 ml of water. A $1 \times 10^{-2}$ M tris(hydroxymethyl)aminomethane (TRIS) buffer containing 0.1 M KCl was prepared by dissolving 1.21 g tris (hydroxymethyl)aminomethane and 7.4 g KCl in approximately 800 ml of deionized water adjusting pH to 7.4 using NaOH then diluting to 1 liter with deionized water. A solution containing $2 \times 10^{-4}$ M $Ca^{+2}$ (8 ppm $Ca^{+2}$) was prepared by dissolving $CaCl_2$ $2H_2O$ in water. Appropriate aliquots of the $2 \times 10^{-4}$ M $Ca^{+2}$ solution were added to 100 ml volumetric flasks. 2 ml of the TRIS buffer was added to the flask along with enough deionized water so that the total volume was approximately 75 ml. Finally, 2 ml of the BAPTA reagent was added along with deionized water. A stable fluorescence had developed when the sample was analyzed. Several samples in the range of 0–3.2 ppm final concentration of $Ca^{+2}$ were analyzed. The excitation was at 295 nm and emission at 365 in a 1.0 cm $\times$ 1.0 cm cuvette. The response is monotonic and fluorescence decreases predictably as calcium is complexed by the BAPTA reagent. The results are summarized below in Table 9. Such data exhibits a coefficient of linear correlation (r) of 0.985.

TABLE 9

| Final Concentration Calcium (ppm) | % Relative Fluorescence Excitation 295, Emission 365 |
|---|---|
| 0 | 100% |
| 0.4 | 99.4% |
| 0.8 | 89.6% |
| 1.6 | 68.7% |
| 2.4 | 43.4% |
| 3.2 | 7.6% |

We claim:

1. A method of regulating the in-system concentration of a water treatment agent in an industrial fluid system comprising:

adding an inert tracer to an industrial fluid system, the inert tracer being added in known proportion to a target specie also being added to said industrial fluid system, wherein the system consumption of the target specie is effected by the water treatment agent;

drawing a sample of fluid from said industrial fluid system;

monitoring the target-specie by analysis of said sample to determine at least one characteristic that can be correlated to an in-system concentration of said target-specie;

monitoring said inert tracer by analysis of said sample to determine the in-system concentration of said inert tracer;

determining the system consumption of the target specie from the measured in-system concentration of the target specie and the inert tracer; and regulating the in-system concentration of the water treatment agent in the fluid system based on the system consumption of the target specie.

2. A method of regulating the in-system concentration of a water treatment agent in an industrial fluid system comprising:

adding an inert tracer to an industrial fluid system, the inert tracer being added in known proportion to a target specie also being added to said industrial fluid system, wherein the system consumption of the target specie is effected by the water treatment agent;

drawing a sample of fluid from said industrial fluid system;

adding to the sample an incipient reagent in an amount effective to convert the target specie to a subject target specie indicator;

monitoring the subject target-specie indicator by analysis of said sample to determine at least one characteristic that can be correlated to an in-system concentration of said target-specie;

monitoring said inert tracer by analysis of said sample to determine the in-system concentration of said inert tracer;

determining the system consumption of the target specie from the measured in-system concentration of the target specie and the inert tracer; and regulating the in-system concentration of the water treatment agent in the fluid system based on the system consumption of the target specie.

3. The method of claim 2 wherein said monitoring of said subject target-specie indicator is performed by fluorescence analysis of said sample to determine at least one fluorescence emission value that can be correlated to said in-system concentration of said target specie indicator.

4. The method of claim 2 wherein said subject target-specie indicator comprises a combination of said incipient reagent and a substantially nonfluorescent target specie, and wherein said correlation of said fluorescence emission value to said in-system concentration of said subject target-specie indicator is established by at least one difference between at least one fluorescence characteristic of said incipient reagent and one fluorescence characteristic of said subject target-specie indicator.

5. The method of claim 2 wherein said monitoring of said subject target-specie indicator is conducted at the site of said industrial system on a substantially continuous basis.

6. The method of claim 2 wherein at least one adjustment of said in-system concentration of said water treatment agent is made based on said system consumption for said target specie.

7. The method of claim 2 wherein said incipient reagent is substantially nonfluorescent and said subject target-specie indicator is fluorescent.

8. The method of claim 2 wherein said incipient reagent is fluorescent and said subject target-specie indicator is substantially nonfluorescent.

9. The method of claim 2 wherein both said incipient reagent and subject target-specie indicator are fluorescent, and wherein said fluorescence analysis is performed using a fluorescence analysis technique that at least minimizes interference between fluorescence emission of any residual incipient reagent and fluorescence emissions of said subject target-specie indicator.

10. The method of claim 2 further including feeding said water treatment agent to said fluid system together with a second inert tracer and monitoring the in-system concentration of said second inert tracer.

11. The method of claim 2 further including feeding said water treatment agent to said fluid system and monitoring the zero-consumption concentration of said water treatment agent and said target specie by fluorescence analysis by:

(1) feeding said water treatment agent through a feed line to said fluid system as a component of a treatment product which contains a second inert tracer in known proportion to said water treatment agent; and (2) determining the concentration of said inert tracer and said second inert tracer within said fluid system.

12. The method of claim 2 wherein said target specie is sulfide, calcium, iron, carbonate, copper (bi)carbonate, alkalinity, copper, sulfate, fluoride, magnesium, and phosphate.

13. The method of claim 2 wherein said target specie is sulfide, calcium, iron, carbonate, copper and phosphate.

14. A method of target-specie responsive regulation of water treatment agent in-system concentration in an industrial fluid system comprising:

drawing a sample of fluid from an industrial fluid system containing at least one target specie, wherein said system consumption of the target specie is affected by at least one water treatment agent;

adding to said sample an incipient reagent in an amount effective to convert said target specie to a target-specie indicator which comprises a combination of said incipient reagent and said target specie;

monitoring said target-specie indicator by fluorescence analysis of said sample to determine at least one fluorescence characteristic of said target-specie indicator that can be correlated to the in-system concentration of said target-specie indicator;

correlating said in-system concentration of said target-specie indicator to an in-system concentration of said target specie;

adding an inert tracer to said industrial fluid system in known proportion to the feed of said target specie to said industrial fluid system;

monitoring said inert tracer by analysis of said sample to determine the in-system concentration of said inert tracer;

correlating said in-system concentration of said inert tracer to a zero-consumption concentration of said target specie;

determining the system consumption value for said target specie by subtracting said in-system concentration of said target specie from said zero-consumption concentration of said target specie; and regulating the in-system concentration of a water treatment agent in said fluid system based on said system consumption of the target specie.

15. The method of claim 14 wherein said target-specie is calcium.

16. The method of claim 14 wherein said target-specie indicator is a complex formed between calcium and 1,2-bis(o-aminophenoxy) ethane-N,N,N',N'-tetraacetic acid.

* * * * *